United States Patent [19]

Disteldorf et al.

[11] Patent Number: 4,476,054

[45] Date of Patent: Oct. 9, 1984

[54] URETIDIONE DIMER OF ISOPHORONE DIISOCYANATE AND METHOD OF PREPARATION

[75] Inventors: Josef Disteldorf; Werner Hübel, both of Herne; Elmar Wolf, Recklinghausen, all of Fed. Rep. of Germany

[73] Assignee: Chemische Werke Huls AG, Marl, Fed. Rep. of Germany

[21] Appl. No.: 292,499

[22] Filed: Aug. 13, 1981

[30] Foreign Application Priority Data

Aug. 13, 1980 [DE]  Fed. Rep. of Germany ....... 3030513

[51] Int. Cl.³ ............................................ C07D 229/00
[52] U.S. Cl. ................................. 260/239 A; 544/222
[58] Field of Search ..................................... 260/239 A

[56] References Cited

U.S. PATENT DOCUMENTS 3,290,288  12/1966  Oertel et al. ................... 260/239 A

FOREIGN PATENT DOCUMENTS 1934763  1/1971  Fed. Rep. of Germany .
2420475  11/1975  Fed. Rep. of Germany .
1153815  5/1969  United Kingdom .

*Primary Examiner*—Dolph H. Torrence
*Attorney, Agent, or Firm*—Oblon, Fisher, Spivak, McClelland & Maier

[57] ABSTRACT

A process for producing a substantially isocyanurate-free uretidione dimer of isophorone diisocyanate, which is more than 98% decomposable by heat to isophorone diisocyanate, which comprises dimerizing isophorone diisocyanate, optionally in an inert organic solvent, in the presence of a catalyst of the formula $X_mP(NR_2)_{3-m}$ wherein m=0, 1, 2; X=Cl OR of R wherein R is selected from the group consisting of the same or different aklyl radical, aralkyl radical, cycloalkyl radical, substituted cycloalkyl radical and radicals wherein two or more of the aforementioned radicals form a hererocyclic ring together with the nitrogen atom; at temperatures of 0°–80° C., isolating the resulting 1,3-diazacyclobutane-2,4-dione, after 5–70% conversion, without previous inactivation of the catalyst, from the reaction mixture as the residue of a thin film distillation and isolating the catalyst and monomer as the distillate.

12 Claims, No Drawings

URETIDIONE DIMER OF ISOPHORONE DIISOCYANATE AND METHOD OF PREPARATION

BACKGROUND OF THE INVENTION

1. Field of the Invention

The present invention relates to a method for producing an isocyanurate-free uretidione dimer of 3-isocyanato-methyl-3,5,5-trimethylcyclohexylisocyanate (isophorone diisocyanate, IPDI) as well as the uretidione dimer produced according to this method.

2. Description of the Prior Art

Aromatic substituted uretidiones and their preparation by dimerization of aromatic isocyanates using tertiary amines or phosphines as catalysts have been known for some time. Very surprisingly, however, aliphatic-substituted uretidiones were disclosed for the first time in German OS No. 16 70 720.

The aliphatic uretidiones produced according to the teaching of German OS No. 16 70 720, however, contain considerable amounts of the corresponding isocyanurates as "impurities", (Example 1: about 40% butyl isocyanurate; Example 2a: 49% ethyl isocyanurate, 2b: 59% ethyl isocyanurate, 2C: 79% ethyl isocyanurate).

Also, in dimerizing isophorone diisocyanate as described in German OS No. 16 70 720, no pure uretidione dimer is produced, but rather only a mixture of reaction products containing a maximum of 80% of the uretidione dimer of isophorone diisocyanate. The rest is inseparable isocyanurate derived from isophorone diisocyanate.

German OS No. 1 934 763 deals exclusively with oligomerization of IPDI using tertiary phosphines. The reaction products obtained following the teaching of this Offenlegungsschrift consist of ca. 60 parts by weight (p.b.w.) dimers (decomposable by heat), and ca. 40 p.b.w. trimers or higher oligomers of IPDI (no longer decomposable by heat). The dimer proportion can be increased to ca. 80 p.b.w. by suitable variations of the method (e.g., lower conversion). It is not possible, however, to increase the uretidione content further because the catalyst (tert. phosphine) catalyzes not only the dimerization, but also the trimerization of IPDI to the corresponding isocyanurate.

With the dimerization catalysts of the prior art according to the German OS's Nos. 1 670 720 and 1 934 763 it has not been possible until now to prepare a uretidione dimer of IPDI free of isocyanurate, i.e., a mixture of uretidione and isocyanurate or their higher oligomers was always obtained. Such an isocyanurate-free uretidione dimer of IPDI is of great interest because it makes possible, for the first time, an economical further reaction with diols, for the production of valuable starting materials for polyurethane chemistry.

SUMMARY OF THE INVENTION

Through the present invention a method has now been found for obtaining a highly pure (>98%) uretidione dimer of IPDI.

Accordingly, the object of the invention is a method for producing an isocyanurate-free uretidione dimer of isophorone diisocyanate which is capable of being more than 98% decomposed back into isophorone diisocyanate by heating, characterized in that, isophorone diisocyanate is dimerized, optionally in an inert organic solvent, in the presence of a catalyst of the formula $$X_mP(NR_2)_{3-m}$$

wherein
m=0, 1, 2
X: Cl, OR, or R, and
R: identical or different alkyl, aralkyl, (optionally substituted) cycloalkyl radicals, or the 2 R groups together form a ring with the N atom, at temperatures of 0°–80° C., preferably 10°–30° C., and the resulting 1,3-diazacyclobutane-2,4-dione is isolated from the reaction mixture after 5–70% conversion, preferably 20–50%, without previous deactivation of the catalyst, as the residue of a thin film distillation and the catalyst and monomer are isolated as the distillate.

DESCRIPTION OF THE PREFERRED EMBODIMENTS

The catalysts are used in amounts of 0.01–5% b.w., preferably 0.5–2% b.w. Particularly suitable compounds correspond to the formula $P(NR_2)_3$, wherein R has the meaning recited in the claims, e.g., $P(N(CH_3)_2)_3$. The alkyl groups can be those having 1–8 C-atoms, the aralkyl groups are, e.g., benzyl or phenylethyl; and the cycloalkyl groups are, e.g., cyclohexyl or cyclopentyl.

The preparation of the phosphorous compounds is described in Houben-Weyl, Vol. V, p. 108.

Pure uretidione dimers of isophorone diisocyanate produced according to the invention are another embodiment of the invention; they are available not as a mixture, but rather substantially free of isocyanurate.

The uretidione dimer produced from IPDI according to the invention can contain oligomers, i.e., up to four uretidione rings, but is in any case at least more than 98% decomposable into IPDI.

The method according to the invention proceeds in two steps; wherein
(a) in the first step, dimerization occurs with the help of the described catalyst up to the point in the conversion where the reaction mixture can still be handled in the liquid state at room temperature (ca. 40–60% IPDI conversion), and
(b) in the second step, the non-reacted monomeric IPDI is separated from the reaction product along with the catalyst by thin film distillation.

The IPDI that is distilled off (plus catalyst) can be used again in the reaction.

The reaction temperature is in the range of 0°–80° C., preferably 10°–30° C. At higher temperatures, the catalytic transformation of the uretidione dimer of IPDI into the corresponding isocyanurate is clearly noticeable.

The amount of catalyst needed depends greatly on the type of catalyst used and the temperature. Amounts of 0.05–5% b.w. based on the IPDI used are generally adequate. Preferably 0.5–2% b.w. of phosphorous acid triamide is used. The reaction time, the time in which, for example, 40–60% b.w. of the IPDI is converted, depends (at constant temperature) to a large degree on the concentration and the type of catalyst used. As a rule, it is 8–60 hours. The reaction can be carried out in polar solvents such as esters, chlorinated hydrocarbons, ethers and ketones, or without solvent. It is preferable to work without solvent.

The reaction mixture is worked up by thin film distillation as discussed above, at 125°–150° C. and 0.01–0.5 torr.

The pure uretidione dimer of IPDI produced according to the invention is highly viscous at RT ($>10^6$ mPa.s; at 60° C.: 13 000 mPa.s, at 80° C.: 1,100 mPa.s). Its NCO content is in the range of 16.8–18%; i.e., rather high proportions of oligomeric uretidione derivatives of IPDI must be present in the reaction product. The monomer content is <1%. The NCO content of the reaction product after heating to 180°–200° C. is 37.1–37.7% b.w. NCO.

The IR-spectrum of the uretidione dimer of IPDI, in addition to an intense band at 2,260 cm$^{-1}$ (N=C=O-bond vibration) possesses a very intense broad band at 1,760 cm$^{-1}$ that is assigned to the C=O bond vibration of the uretidinedione ring. The characteristic isocyanurate ring bands at 1,690 cm$^{-1}$ do not appear.

The uretidione dimer of IPDI finds applications as an intermediate in the manufacture of plastics, enamels and foam materials. Accordingly, it is particularly valuable, because, due to its low vapor pressure, it is physiologically harmless, and because it makes it possible to liberate the isocyanate groups masked in the uretidione ring by application of higher temperatures.

The product is particularly well suited for the production of solvent-containing and low-solvent single and dual component enamels, such as coil coating and high solid enamels; it is also useful for solvent-free single and dual component coatings.

EXAMPLE 1

200 kg of isophorone diisocyanate and 2 kg of tris(-dimethylamino)phosphine were caused to react in a reactor at room temperature for 24 hours. After this time, the NCO content of the reaction mixture was ca. 30%. Without first deactivating the catalyst, this mixture was worked up in a thin film evaporator. The distilled isophorone diisocyanate, which contained the catalyst nearly quantitatively, was replenished with fresh isophorone diisocyanate up to 200 kg, again allowed to stand until the NCO content was 30%, and then subjected again to thin film evaporation.

An apparatus having two thin film evaporators connected in series was used to separate the unconverted isophorone diisocyanate from the uretidinedione dimer of isophorone diisocyanate. The following conditions have proven optimal for isophorone diisocyanate separation.

|  | Evaporator I | Evaporator II |
|---|---|---|
| Input | 33 l/hr · m$^2$ output | |
| Hot oil-inflow | 154° C. | 156° C. |
| Hot oil-outflow | 150° C. | 155° C. |
| Vacuum | 5.8 torr | 0.03 torr |
| Distillate (% of the input) | ca. 34% | ca. 35% |
| Reaction product NCO content | 17.5% | |
| NCO content after heating to 180° C., ½ hour | 37.5%* | |
| Viscosity at RT | $>10^6$ mPa.s | |
| at 40° C. | 125 · 10$^3$ mPa.s | |
| at 60° C. | 13 · 10$^3$ mPa.s | |
| Color | Colorless to light yellow | |

*content of uretidione dimer of isophorone diisocyanate >99%

EXAMPLE 2

1000 p.b.w. of isophorone diisocyanate and 20 p.b.w. of tris(dimethylamino)phosphine were allowed to stand for 10 hours at room temperature. During this time the NCO content fell from 37.8% (pure isophorone diisocyanate) to ca. 31%. Without first inactivating the catalyst the reaction mixture was distilled at 140° C./0.1 torr in a thin film evaporator. The residue had an NCO content of 17.1%; when heated to 180° C. (½ hour) an NCO content of 37% was found.

EXAMPLE 3

1000 p.b.w. of isophorone diisocyanate and 20 p.b.w. of phosphorous acid bis(dimethylamide)chloride were mixed and allowed to stand 30 hours at room temperature. After this time the NCO content of the reaction mixture was 32.5% NCO. It was worked up as in Example 2. The residue contained 16.8% NCO; when heated to 180° C. (½ hour) an NCO content of 37.2% was found.

EXAMPLE 4

1000 p.b.w. of isophorone diisocyanate and 20 p.b.w. of phosphorous methylester-bis(diethylamide) were mixed and allowed to stand 40 hours at room temperature. After this time the NCO content of the reaction mixture was 33.2%. It was worked up as in Example 2. The residue contained 17.0% NCO; when heated to 180° C. (½ hour) an NCO content of 37.7% was found.

EXAMPLE 5 (COMPARATIVE EXAMPLE)

1000 p.b.w. of isophorone diisocyanate and 10 p.b.w. of tributylphosphine were allowed to stand in a reactor at room temperature. Since no noticeable reaction heat was evolved, stirring was not necessary. After 40 hours, the NCO content of the reaction mixture was ca. 30% NCO (=45% isophorone diisocyanate conversion).

The reaction mixture, which was still of low viscosity, was added to the thin film distillation apparatus without previously deactivating the catalyst. Isophorone diisocyanate was distilled from the reaction product at 135° C./0.1 torr. The residue had an NCO content of 17.4% NCO. When the residue was heated to 180° C. (½ hour) the NCO content was 33.5%, i.e., the reaction product consisted of ca. 20 p.b.w. of trimer of isophorone diisocyanate, and ca. 80 p.b.w. of heat decomposable derivative of isophorone diisocyanate.

We claim:

1. A process for producing a substantially isocyanate-free uretidione dimer of isophorone diisocyanate, which is more than 98% decomposable by heat to isophorone diisocyanate, which comprises:

dimerizing isophorone diisocyanate in the presence of a catalyst of the formula

$$X_mP(NR_2)_{3-m}$$

wherein
m=0, 1, or 2,
X=Cl, OR or R, and
R is selected from the group consisting of the same or different C$_1$–C$_8$-alkyl radical, benzyl radical, phenylethyl radical, cyclohexyl radical, and cyclopentyl radical, at temperatures of 0°–80° C., isolating the resulting 1,3-diazacyclobutane-2,4-dione after 5–70% conversion, without previous inactivation of the catalyst, from the reaction mixture as the residue of a thin film distillation and isolating the catalyst and monomer as the distillate of said distillation.

2. The process of claim 1 wherein said dimerization reaction is carried out at 10°–30° C.

3. The process of claim 1 wherein said isolation is carried out after 20–50% conversion has occured.

4. The process of claim 1 wherein said catalyst has the formula $$P(NR_2)_3$$

and is present in an amount of 0.01–5% by weight.

5. The process of claim 4 wherein said catalyst is present in an amount of 0.5–2% by weight.

6. The process of claim 1 or 4 wherein said catalyst has the formula $$P(N(CH_3)_2)_3.$$

7. The process of claim 1 wherein any unreacted isophorone diisocyanate recovered from the reaction mixture is returned to the reaction mixture.

8. The process of claim 1 wherein R is methyl or ethyl.

9. An uretidione dimer of isophorone diisocyanate which is substantially free of isocyanurate and which is more than 98% decomposable by heat to isophoronediisocyanate.

10. The uretidione dimer of claim 9 which has an NCO content of 16.8–18%.

11. The uretidione dimer of claim 9 wherein the content of monomeric IPDI is less than 1% by weight.

12. The uretidione dimer prepared by the process of claim 7.

* * * * *